(12) United States Patent
Schlottmann et al.

(10) Patent No.: US 11,134,974 B2
(45) Date of Patent: Oct. 5, 2021

(54) SURGICAL SHAVING INSTRUMENTS

(71) Applicant: GYRUS MEDICAL LIMITED, Cardiff (GB)

(72) Inventors: Ole Schlottmann, Cardiff (GB); David Morris, Rhondda (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 0 days.

(21) Appl. No.: 16/251,808

(22) Filed: Jan. 18, 2019

(65) Prior Publication Data

US 2019/0239912 A1 Aug. 8, 2019

(30) Foreign Application Priority Data

Feb. 2, 2018 (GB) .................................... 1801738

(51) Int. Cl.
| | |
|---|---|
| *A61B 17/32* | (2006.01) |
| *B24B 3/60* | (2006.01) |
| *A61B 18/14* | (2006.01) |
| *A61B 17/00* | (2006.01) |

(52) U.S. Cl.
CPC .... *A61B 17/32002* (2013.01); *A61B 18/1482* (2013.01); *B24B 3/60* (2013.01); *A61B 2017/0088* (2013.01); *A61B 2017/320008* (2013.01); *A61B 2017/320032* (2013.01)

(58) Field of Classification Search
CPC ...... A61B 17/320016; A61B 17/32002; A61B 17/3207; A61B 17/320758–2017/320791
See application file for complete search history.

(56) References Cited

U.S. PATENT DOCUMENTS

| | | | | |
|---|---|---|---|---|
| 4,850,354 | A | * | 7/1989 | McGurk-Burleson ....................... A61B 17/32002 606/170 |
| 5,741,287 | A | * | 4/1998 | Alden .............. A61B 17/32002 604/22 |
| 6,217,598 | B1 | | 4/2001 | Berman et al. |
| 2005/0065538 | A1 | * | 3/2005 | Van Wyk ......... A61B 17/32002 606/159 |

(Continued)

FOREIGN PATENT DOCUMENTS

WO 2006/102124 A2 9/2006

OTHER PUBLICATIONS

Jul. 10, 2018 Search Report issued in European Patent Application No. GB1801738.4.

*Primary Examiner* — Darwin P Erezo
*Assistant Examiner* — Brigid K Byrd
(74) *Attorney, Agent, or Firm* — Oliff PLC

(57) ABSTRACT

A surgical shaving instrument (1) comprises a main body (2), a hollow elongate shaft (4) extending from the main body (2). The elongate shaft (4) defines an elongate inner open volume through the shaft. A tip portion (18) extends from the distal end region of the elongate shaft (4). A driveshaft extends through the elongate shaft (4) from the main body (2) to the distal end region of the elongate shaft (4). A cutter head (12) is attached to the driveshaft and located in the tip portion (10), the cutter head (12) extends at least partially out of the tip portion (18). The aperture of the tip portion (18) is defined by an inner edge, and a portion of the inner edge defines a fixed shaver blade (40) for the instrument, the fixed shaver blade (40) having a cutting angle which is substantially constant along the inner edge.

10 Claims, 7 Drawing Sheets

(56) References Cited

U.S. PATENT DOCUMENTS

| | | | |
|---|---|---|---|
| 2006/0095055 A1* | 5/2006 | Douglas | A61B 17/32 606/159 |
| 2006/0212060 A1* | 9/2006 | Hacker | A61B 17/320016 606/180 |
| 2008/0188848 A1* | 8/2008 | Deutmeyer | A61B 18/1485 606/40 |
| 2014/0277040 A1* | 9/2014 | Hayes | A61B 17/32002 606/170 |

* cited by examiner

SURGICAL SHAVING INSTRUMENTS

The present invention relates to surgical shaving instruments, and, in particular, to arthroscopic surgical instruments.

BACKGROUND OF THE INVENTION

Surgical shaving instruments are used by surgeons to perform surgical resection operations. Such instruments are also known bone burrs, or bone shavers. One particular type of instrument uses a rotating or oscillating cutting head mounted at a distal end of a hollow elongate shaft. The cutting head is typically driven by a motor or other drive means located in a device body from which the shaft extends. The cutting head is mounted on a driveshaft that extends through the elongate shaft. A distal tip portion of the elongate shaft provides a cutting window through which a portion of the cutting head extends for engagement with the tissue to be cut. Loose tissue (debris from the shaving action) can be removed from the cutting zone through the hollow elongate shaft, or by suction or some other means.

The distal tip portion can also be provided with, or define, a fixed cutting blade for manual cutting of tissue. Existing designs of fixed cutting blade have been found not to be optimal, and, accordingly, it is desirable to provide a design of instrument that provides an improved cutting blade.

SUMMARY OF THE INVENTION

Aspects of the present invention are set out in the attached claims.

According to one aspect of the present invention, there is provided a surgical shaving instrument comprising a main body; a hollow elongate shaft extending from the main body, the shaft defining an elongate inner open volume which extends from a proximal end region to a distal end region of the shaft; a tip portion extending from the distal end region of the elongate shaft, and defining a tip cavity therein, the tip portion having an outer surface which defines an aperture therethrough into the tip cavity, such that the tip cavity is open; a driveshaft which extends through the inner open volume of the elongate shaft from the main body to the distal end region of the elongate shaft; and a cutter head attached to the driveshaft and located in the tip cavity of the tip portion, the cutter head extending at least partially out of the tip portion through the aperture, wherein the aperture of the tip portion is defined by an inner edge, and a portion of the inner edge defines a fixed shaver blade for the instrument, the fixed shaver blade having a cutting angle which is substantially constant along the inner edge.

In one example, the driveshaft defines an elongate lumen therethrough.

In one example, the tip portion has an outer surface, and an inner surface adjacent the tip cavity, the cutting angle of the fixed shaver blade being defined between the inner and outer surfaces of the tip portion.

In one example, the tip portion is of an electrically insulating ceramic material. One such example may further comprise an electrically conductive electrode on at least part of that outer surface.

In one example, the shaver blade has a cutting angle substantially in a range of 5° to 40°.

One example comprises drive means located in the main body for driving the cutter head via the driveshaft. The drive means may be operable to oscillate and/or rotate the driveshaft.

One example may comprise control means located in the main body for controlling drive of the cutter head.

DETAILED DESCRIPTION OF THE PREFERRED EMBODIMENTS

Figure 1:
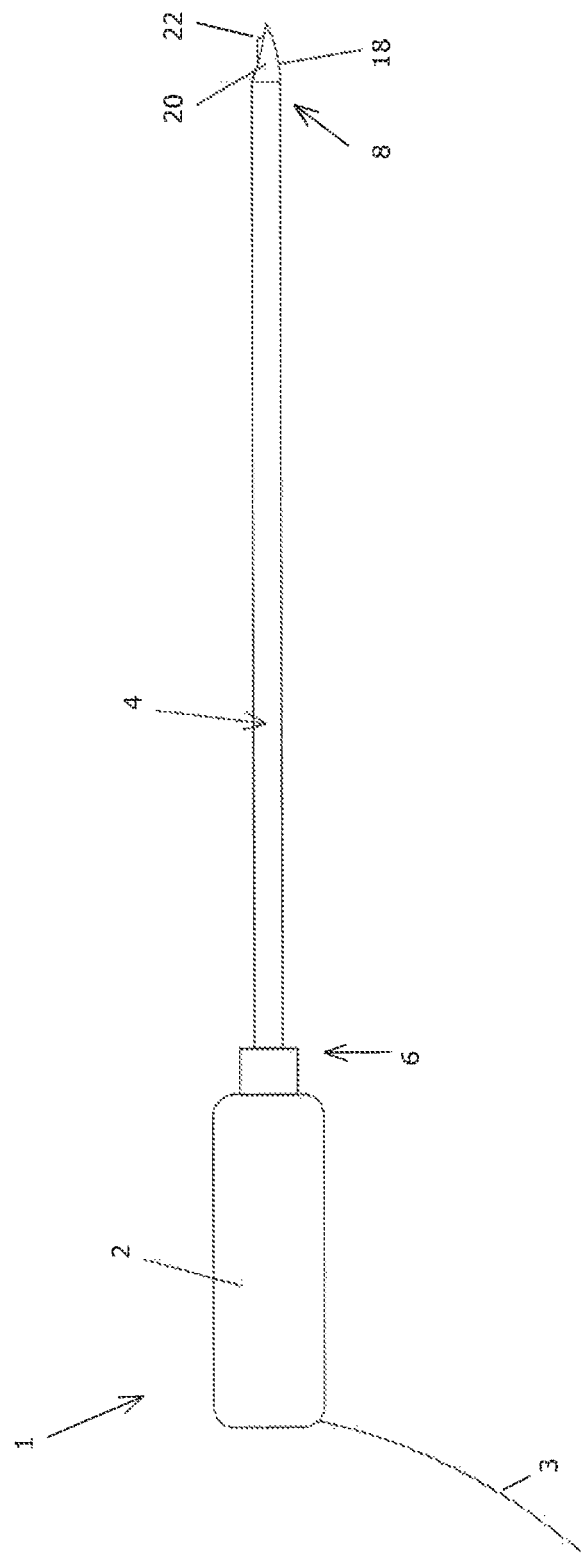
FIG. 1 is a schematic side view of a surgical shaving instrument.

A surgical shaving instrument 1 is shown schematically in FIG. 1, and comprises a body 2 in which is located a drive unit and control means, for example control circuitry. The control means receives electrical power and control signals via a power and control connection 3, and may receive control signals from appropriately located control inputs, such as buttons or switches. Such control inputs may be located on the body 2, and/or in a suitable location for the user. The drive unit may include and electrical motor and/or oscillator.

Figure 2:
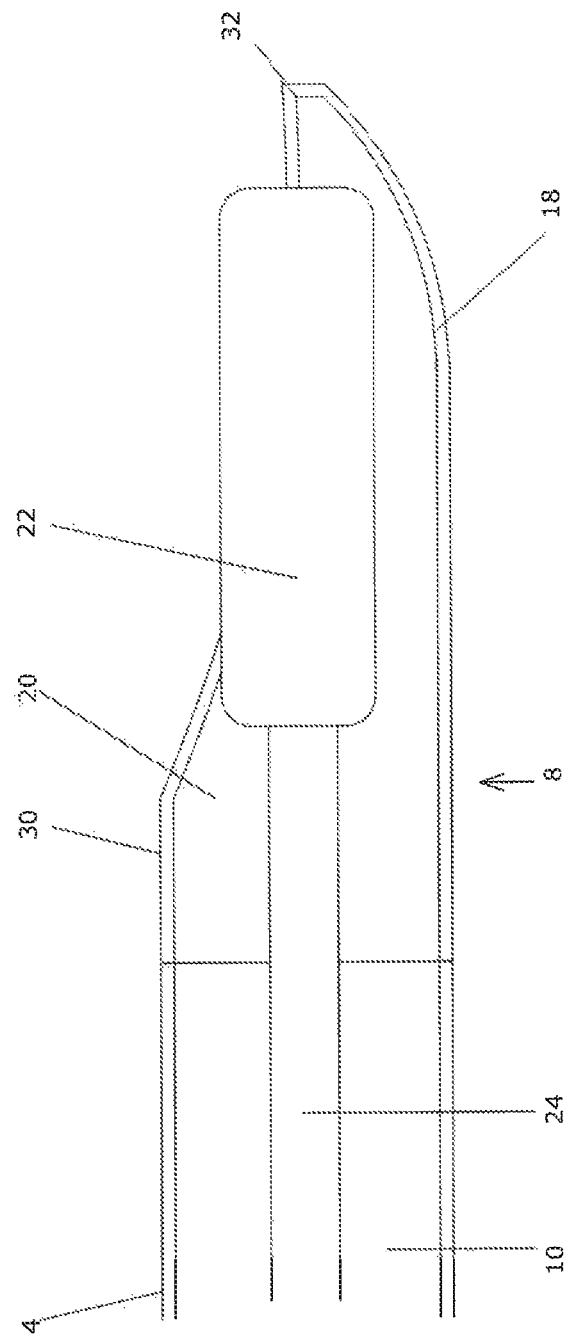
FIG. 2 is a schematic cross-sectional side view of a distal end portion of the instrument of FIG. 1.
Figure 3:
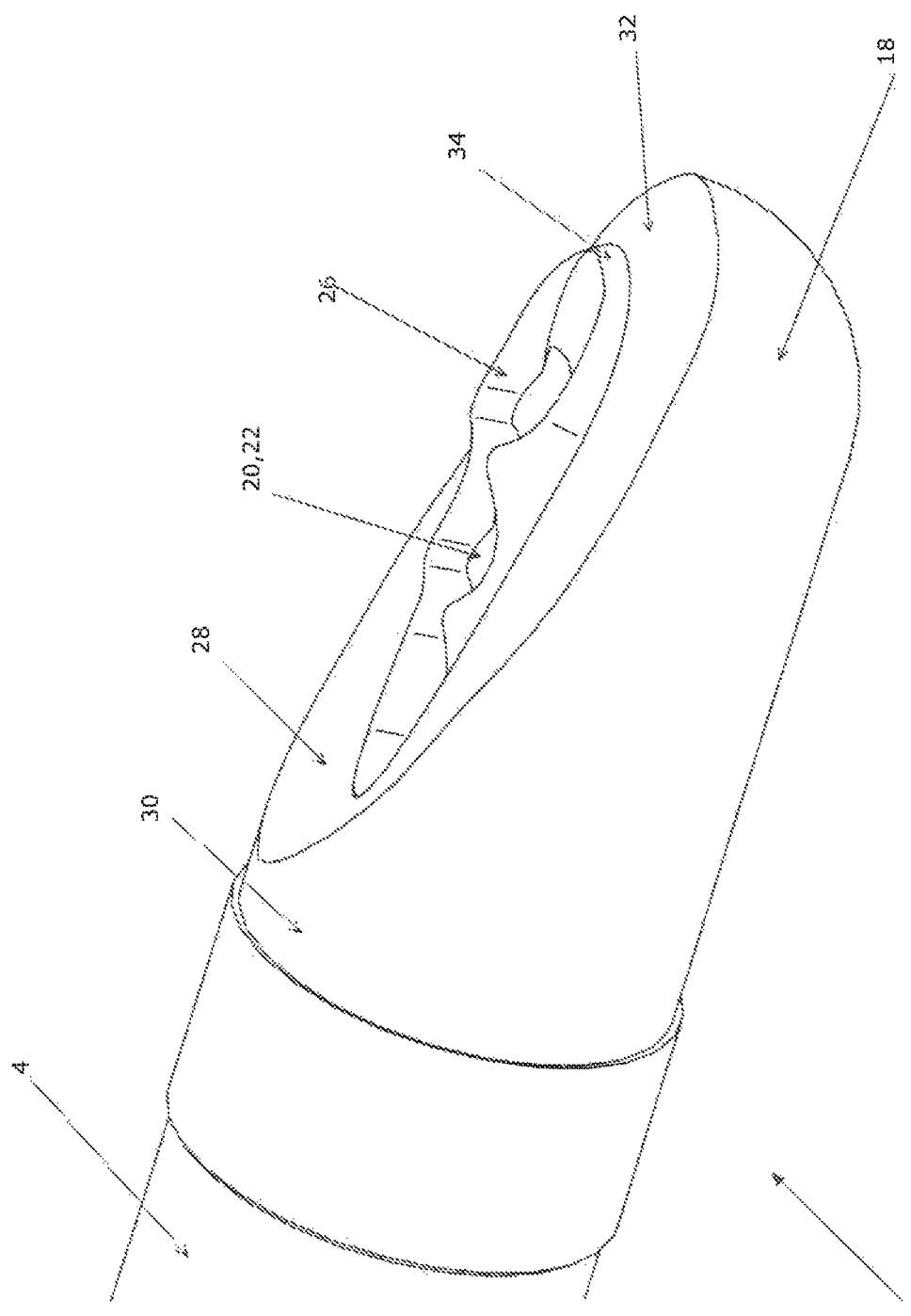
FIG. 3 is a schematic perspective view of a first example distal end portion of the instrument of FIGS. 1 and 2 embodying one aspect of the present invention.

A distal end of the instrument of FIG. 1 is shown in more detail, in cross-sectional view, in FIG. 2, and a schematic perspective view of a first example distal end region is shown in FIG. 3.

With reference to FIGS. 1 to 3, a hollow elongate shaft 4 extends from the body 2 from a proximal end region 6 to a distal end region 8 of the elongate shaft 4. The elongate shaft 4 extends along a longitudinal axis, and defines an inner open volume 10 therealong. The distal end region 8 carries a tip portion 18, which defines an inner tip cavity 20 contiguous with the inner open volume 10 of the elongate shaft 4. A cutting head 22 is located in the tip cavity 20. The cutting head 22 is driven by the drive unit of the body 2 via a driveshaft 24 that extends through the inner open volume 10 of the elongate shaft 4. The tip portion 18 defines an aperture 26 through a surface 28 of the tip portion 18. The outer surface 28 of the tip portion 18 that defines the aperture 26 is, in this example, a convex surface that extends from a first end region 30 of the tip portion 18 to a narrowed second end region 32 of the tip portion 32. The second end region 32 forms a distal tip of the instrument 1. The cutting head 22 extends at least partially through the aperture 26 so as to be able to contact tissue.

In one example, the driveshaft 24 is hollow, and defines an elongate lumen therealong. The cutting head 22 is also hollow, and is arranged to be contiguous with the lumen of the driveshaft 24. In use, tissue material removed by the cutting head 22 can be retrieved through the cutting head 22, and along the lumen of the hollow driveshaft 24, for removal.

The tip portion 18 may be metallic or may be of a ceramic non-electrically conductive (electrically insulating) material, such as an alumina, a zirconia, a carbide or a nitride when an electrode is provided.

In accordance with an aspect of the present invention, the tip portion 18 defines a fixed shaver blade 34 on a distal edge region of the aperture 26 through the surface 28. This fixed shave blade 34 is used by the surgeon for manual removal of tissue, sometimes to be broken up and removed by the cutter head 12. The fixed shaver blade 34 is directed towards the elongate shaft 4 from the distal end of the tip portion 18 so that cutting is ached by pulling of the instrument 1 towards the operator.

Figure 4:
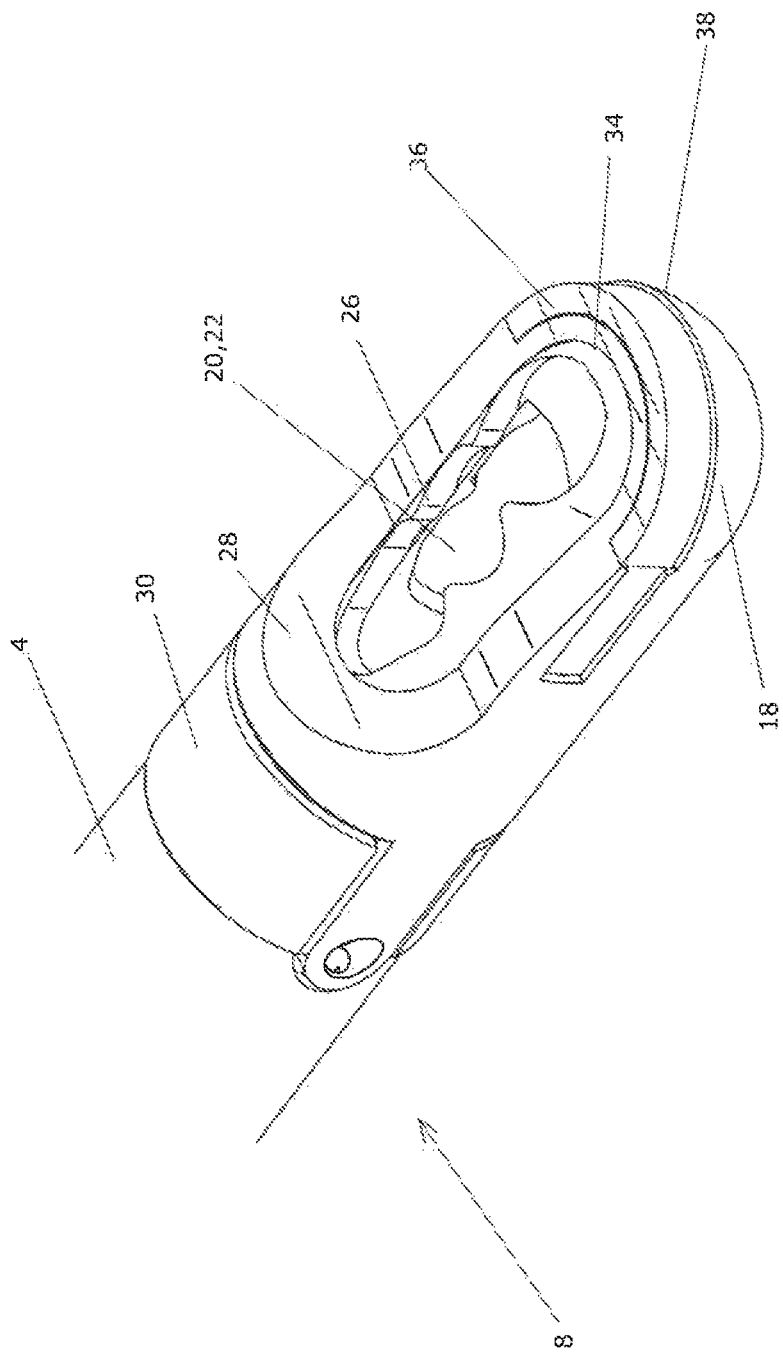
FIG. 4 is a schematic perspective view of a second example distal end portion of the instrument of FIGS. 1 and 2 embodying one aspect of the present invention.
Figure 5:
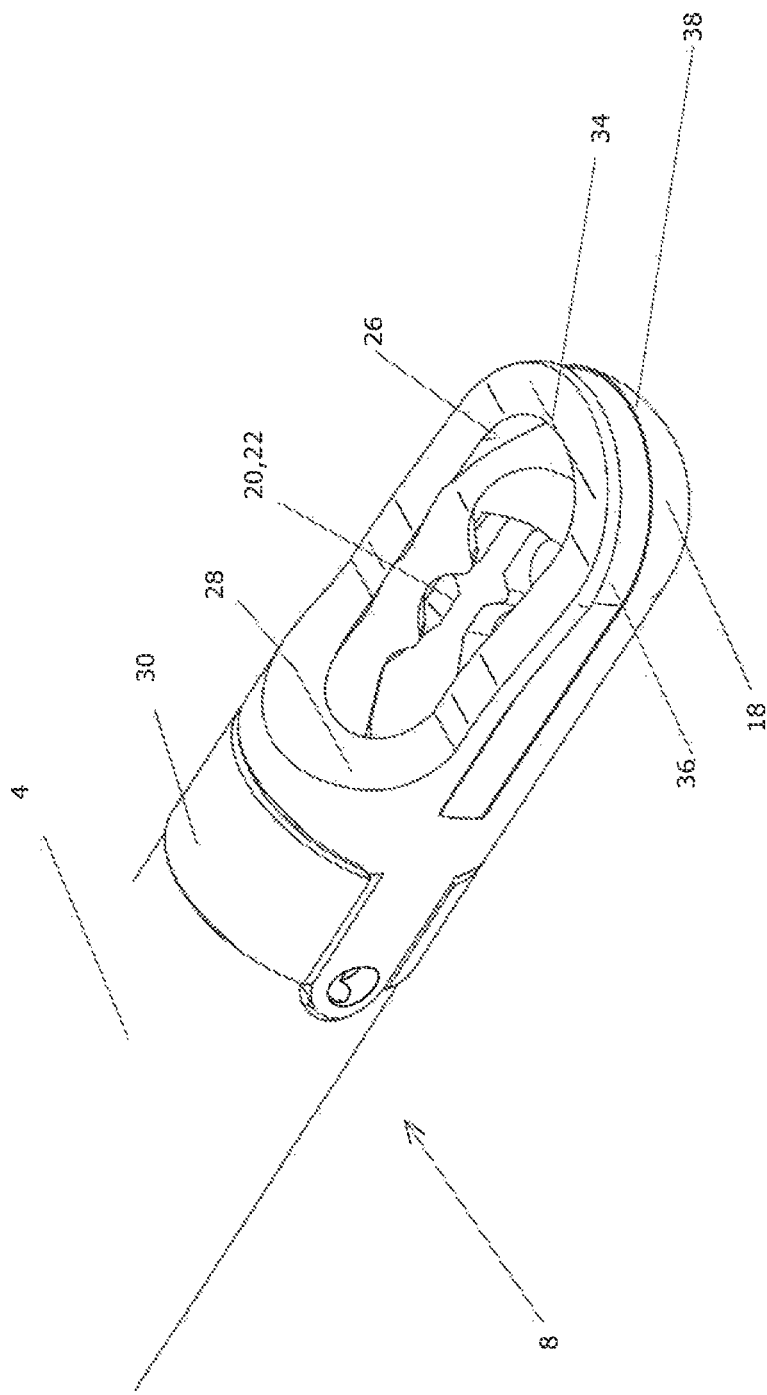
FIG. 5 is a schematic perspective view of a third example distal end portion design of the instrument of FIGS. 1 and 2 embodying one aspect of the present invention.

FIGS. 4 and 5 illustrate respective second and third example designs of the end region 8 of an instrument embodying the present invention. In the example of FIGS. 4 and 5, the tip portion 18 carries an optional electrically conductive electrode 36 on an outer region 38 thereof. This position for the electrode 36 allows for good contact with tissue being treated. In use, the electrode 36 is supplied with radio frequency electrical signals in order to provide coagulation and/or ablation function for the instrument 1. The radio frequency signals are provided from an RF generator, and supplied to the electrode 36 via the control circuitry in the body 2 of the instrument 1, in accordance with known practice for such coagulation and/or ablation functions. Detailed description of such function is omitted here for the sake of brevity.

As in the first example, the tip portion 18 may be metallic or may be of a ceramic non-electrically conductive (electrically insulating) material, such as an alumina, a zirconia, a carbide or a nitride when an electrode is provided. A non-electrically conductive material serves to insulate such an electrode 36 from the metallic, electrically conductive elongate shaft 4, thereby enabling the provision of the radio frequency coagulation and ablation function provided by the electrode 36.

In each of the first, second and third example, and in accordance with an aspect of the present invention, the tip portion 18 defines a fixed shaver blade 34 on a distal edge region of the aperture 26 through the surface 28. This fixed shave blade 34 is used by the surgeon for manual removal of tissue, sometimes to be broken up and removed by the cutter head 12. The fixed shaver blade 34 is directed towards the elongate shaft 4 from the distal end of the tip portion 18 so that cutting is ached by pulling of the instrument 1 towards the operator.

Figure 6:
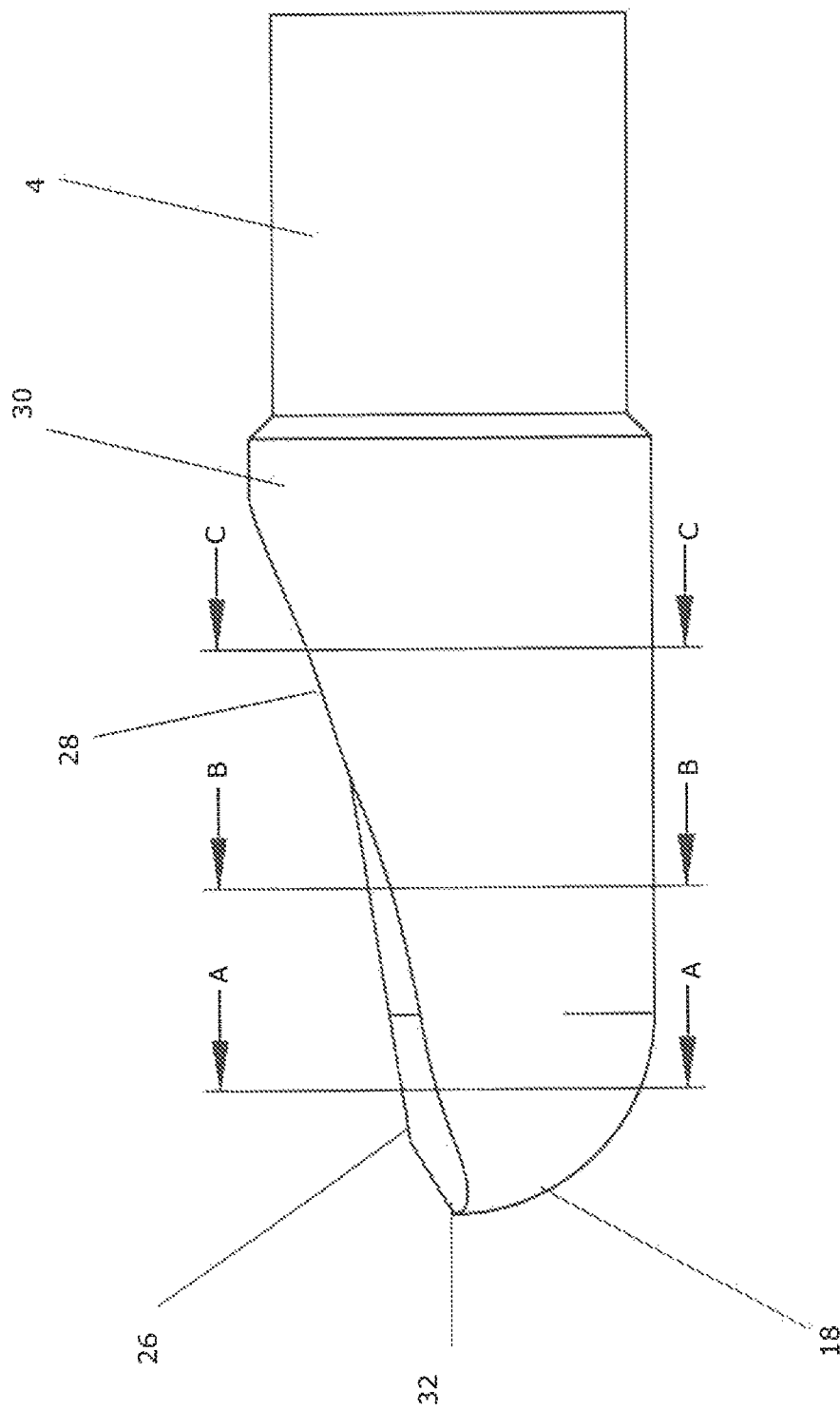
FIG. 6 is a simplified schematic side view of the distal end portion of FIG. 3, 4 or 5.

FIG. 6 illustrates a schematic simplified side view of the end region 8. As before, the tip portion 18 has a first end region 30 that extends from the shaft 4. The tip portion 18 defines the fixed shaver blade 34. In accordance the present invention, the fixed shaver blade is defined by an inner edge of the ceramic tip portion 18. The inner edge is defined between the outer and inner surfaces of the tip portion, the inner surface being adjacent the tip cavity 20.

Figure 7A:
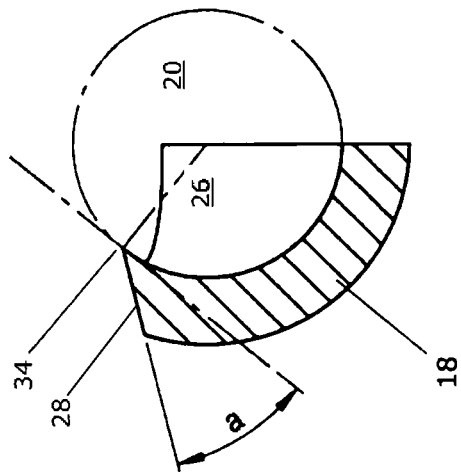
FIGS. 7A to 7C are schematic longitudinal cross-sectional end views of the distal end portion of FIG. 6.
Figure 7B:
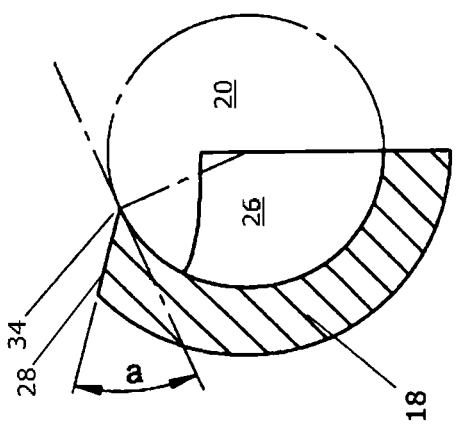
Figure 7C:
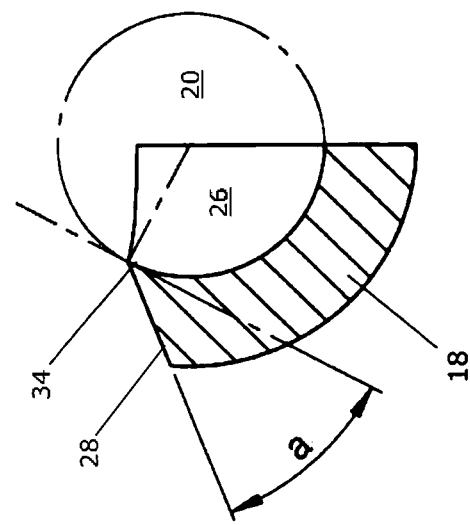

FIGS. 7A, 7B and 7C show respective longitudinal cross sections taken along section lines A-A, B-B, and C-C, and illustrate how the outer surface angle changes along the length of the tip portion 18, so that the cutting edge angle a of the fixed shaver blade remains substantially constant along that length. The inner surface is substantially circular in longitudinal cross-section, so as to define a cavity having a circular longitudinal cross-section. The outer surface 28 extends at least partially transversely across the tip portion 18, so as to define the aperture 26 through the tip portion 18 to allow access into the inner cavity 20 of the tip portion 18. Accordingly, in order to maintain a substantially constant cutting edge angel, the angle of the outer surface 28 varies with respect to the longitudinal access of the instrument, along the length of the outer surface 28.

The fixed shaver blade 34 has a substantially constant acute cutting edge angle a, for example in the range of 5° to 40° depending on the requirements of the instrument. This sharper fixed shaver blade 34 allows for the reduction of cutting speed, torque and power requirements of the cutter head 12, which results in the ability to provide a smaller drive unit in the body 2 of the instrument 1. This size reduction then allows the instrument to be reduced in size, and may then be provided as a one-piece instrument.

The manufacture of the tip portion 18 of a ceramic material provides the additional benefit that the fixed shaver blade 34 is typically more durable (from the edge perspective) than if provided by a metallic material.

The invention claimed is:

1. A surgical shaving instrument comprising:
   a main body;
   a hollow elongate shaft extending from the main body, the shaft defining an elongate inner open volume which extends from a proximal end region to a distal end region of the shaft;
   a tip portion extending from the distal end region of the elongate shaft, and defining a tip cavity therein, the tip portion having an aperture defined by an innermost edge of an outer surface of the tip portion such that an entirety of the aperture is defined by the innermost edge;
   a driveshaft which extends through the inner open volume of the elongate shaft from the main body to the distal end region of the elongate shaft; and
   a cutter head attached to the driveshaft and located in the tip cavity of the tip portion, wherein:
   the cutter head extends at least partially out of the tip portion through the aperture;
   the innermost edge defines a fixed shaver blade for the instrument; and
   the fixed shaver blade has a cutting angle which is substantially constant along an entirety of the innermost edge.

2. A surgical shaving instrument as claimed in claim 1, wherein the driveshaft defines an elongate lumen therethrough.

3. A surgical shaving instrument as claimed in claim 1, wherein the tip portion has an inner surface adjacent the tip cavity, the cutting angle of the fixed shaver blade being defined between the inner and outer surfaces of the tip portion.

4. A surgical shaving instrument as claimed in claim 1, wherein the tip portion is of an electrically insulating ceramic material.

5. A surgical shaving instrument as claimed in claim 4, further comprising an electrically conductive electrode on at least part of the outer surface of the tip portion.

6. A surgical shaving instrument as claimed in claim 1, wherein the shaver blade has a cutting angle substantially in a range of 5° to 40°.

7. A surgical shaving instrument as claimed in claim 1, further comprising drive means located in the main body for driving the cutter head via the driveshaft.

8. A surgical shaving instrument as claimed in claim 7, wherein the drive means is operable to oscillate the driveshaft.

9. A surgical shaving instrument as claimed in claim 7, wherein the drive means is operable to rotate the driveshaft.

10. A surgical shaving instrument as claimed in claim 1, further comprising control means located in the main body for controlling drive of the cutter head.

* * * * *